(12) United States Patent
Shoemaker, Jr.

(10) Patent No.: US 11,389,623 B1
(45) Date of Patent: Jul. 19, 2022

(54) MEDICAL SLEEVE WITH INTERVENOUS ACCESS DOOR

(71) Applicant: STEPHEN P. SHOEMAKER TRUST, Manhattan Beach, CA (US)

(72) Inventor: Stephen P. Shoemaker, Jr., Redondo Beach, CA (US)

(73) Assignee: Stephen P. ShoemakerTrust, Manhattan Beach, CA (US)

( * ) Notice: Subject to any disclaimer, the term of this patent is extended or adjusted under 35 U.S.C. 154(b) by 0 days.

(21) Appl. No.: 17/396,587

(22) Filed: Aug. 6, 2021

(51) Int. Cl.
*A61M 25/02* (2006.01)

(52) U.S. Cl.
CPC ..... *A61M 25/02* (2013.01); *A61M 2025/0246* (2013.01); *A61M 2205/0272* (2013.01)

(58) Field of Classification Search
CPC .......... A61M 25/02; A61M 2025/0246; A61M 2205/0272

USPC .......................................................... 604/174
See application file for complete search history.

(56) References Cited

U.S. PATENT DOCUMENTS 5,131,412 A * 7/1992 Rankin ................. A61M 25/02
128/877
2021/0212658 A1* 7/2021 McGrath ................ A61B 34/25

* cited by examiner

*Primary Examiner* — Phillip A Gray
(74) *Attorney, Agent, or Firm* — Fulwider Patton LLP

(57) ABSTRACT

A protective medical sleeve for use with a patient having an intravenous flow that permits easy and quick inspection of the site of the injection, but provides protection and a more sanitary environment for the IV site. The thin-walled tubular element includes a convenient door that provides access to the IV site when needed, and can be closed to prevent contaminants from entering the injection site.

3 Claims, 5 Drawing Sheets

MEDICAL SLEEVE WITH INTERVENOUS ACCESS DOOR

BACKGROUND

The present invention relates generally to a protective medical sleeve, and more particularly to a semi-rigid tubular sleeve adapted to slide over a patient's forearm and including a hinged door that maintains a sterile area while permitting access to an IV or wound when needed.

When a patient is hospitalized or when a person is being transported by ambulance to a hospital, the patient may receive an intravenous injection at his or her wrist or forearm. In most of these cases, the patient's arm is typically unprotected and subjected to the surrounding environment. In some cases, this can be either non-sterile or unsanitary until the patient can be transported to a more sterile environment or because there is a long period of time that the IV is attached. Because the IV can be in place for several days or more, the patient will have to sleep with the needle inside the patient's forearm, which can be uncomfortable and problematic if the patient moves or disturbs the IV during sleep. There is nothing currently that can help protect the injection site from the surrounding environment and the risk of detachment during sleep, touching or scratching the area, or inadvertent movement. The present invention is directed to a device to protect a patient with an IV or other medical device and present a more sanitary environment for the patient and the physician.

SUMMARY OF THE INVENTION

The present invention is a substantially rigid or semi-rigid tube sized to fit over a patient's forearm to cover the wrist and forearm. The sleeve preferably has some flexibility and space for comfort and fit, and is made of a durable sterilizable material such as polyvinyl chloride (PVC), stainless steel tubing, etc. that can be easily sanitized and reused as necessary. Located at a middle area of the sleeve is a hinged door that can be opened when the sleeve is on a patient. This allows access to the wrist and forearm, especially where an IV would be located. The hinged door can be open to clean a wound, replace an IV, check for infection or other medical needs, and to air out the skin surface. When closed, the door and the sleeve protects the patient from dislodging the IV and keeps the area sanitary.

These and other features of the invention will best be understood with reference to the accompanying drawings listed below in conjunction with the detailed description of the invention set forth below.

DETAILED DESCRIPTION OF THE PREFERRED EMBODIMENTS

The present invention protects the crux of a patient's elbow when an IV or other medical intrusion is present. When a patient is in need of an IV, the vein or artery is pierced with a needle and flexible tubing is attached with connection for intravenous medication or other needs. The needle and the puncture are open to the environment and can become tangled or dislodged, crimped by a bent elbow, particularly during sleep. The IV tube can become crimped or dislodged as the arm bends and in some cases movement of the arm can cause pain due to movement of the needle or stoppage of IV flow. If the needle should become dislodged or the flow of medicine ceased due to crimping or blockage, the patient could be at serious risk.

Figure 1:
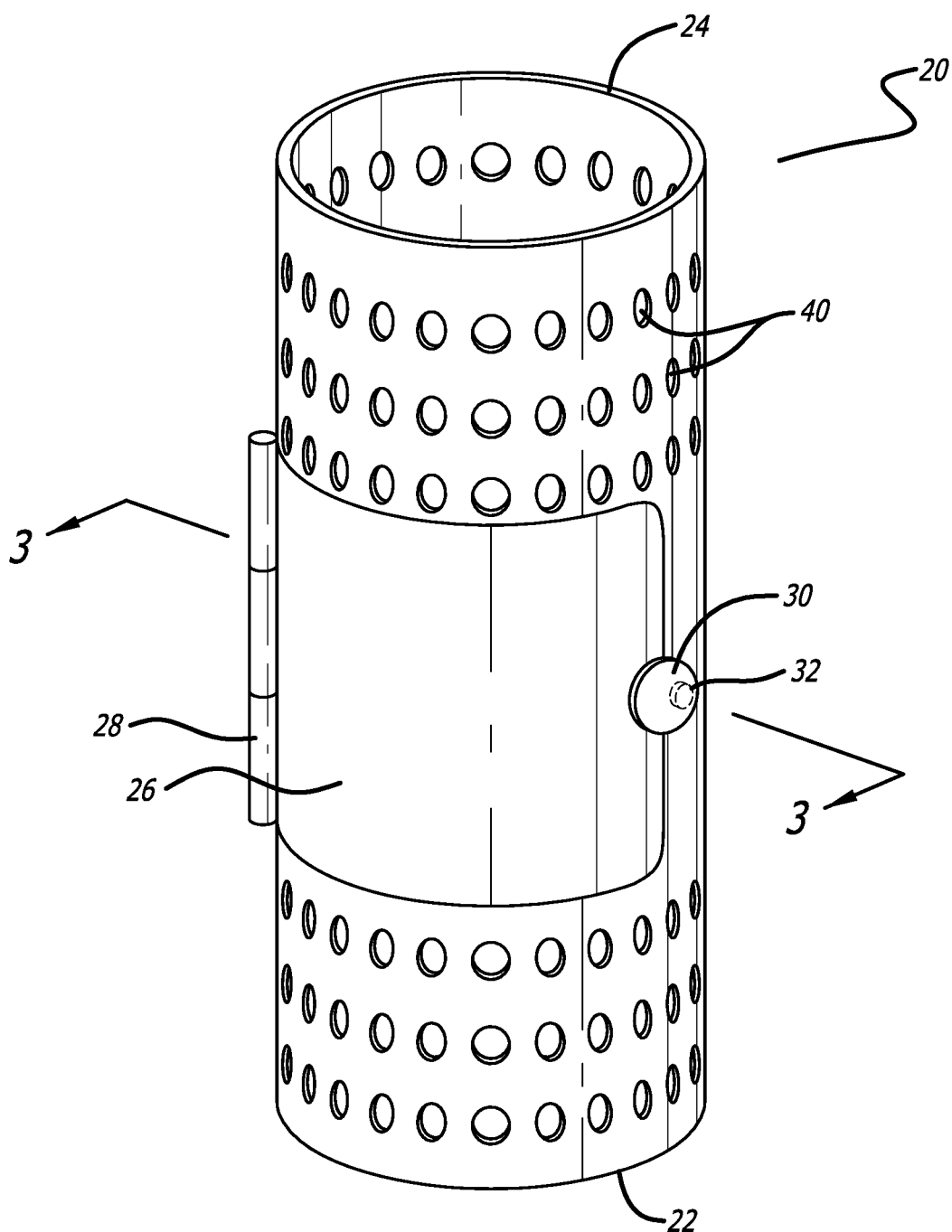
FIG. 1 is an elevated, perspective view of a first preferred embodiment of the present invention in a closed configuration.
Figure 2:
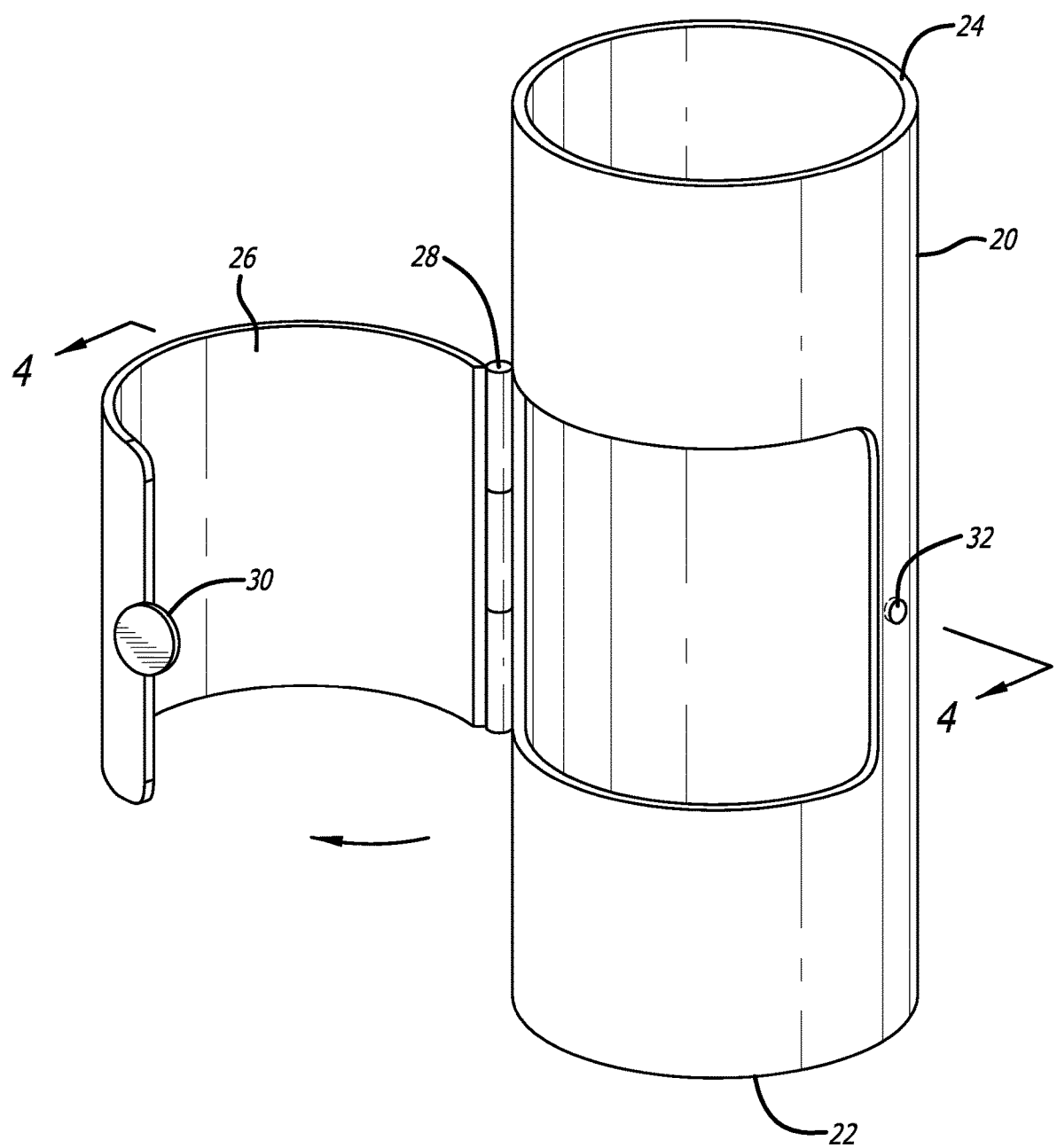
FIG. 2 is an elevated, perspective view of the embodiment of FIG. 1 in the open configuration.
Figure 3:
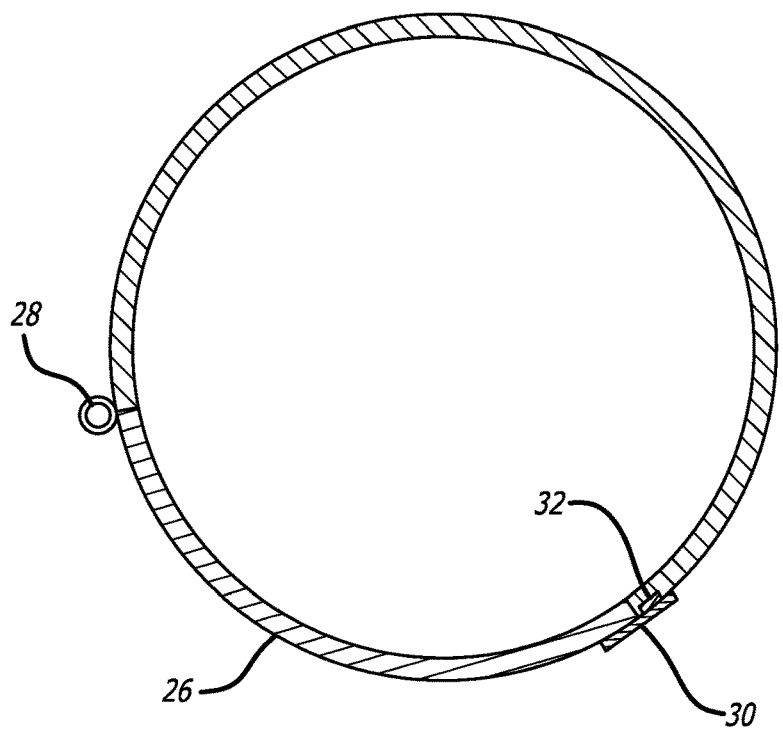
FIG. 3 is a cross sectional view of the embodiment of FIG. 1 taken along line 3-3.
Figure 4:
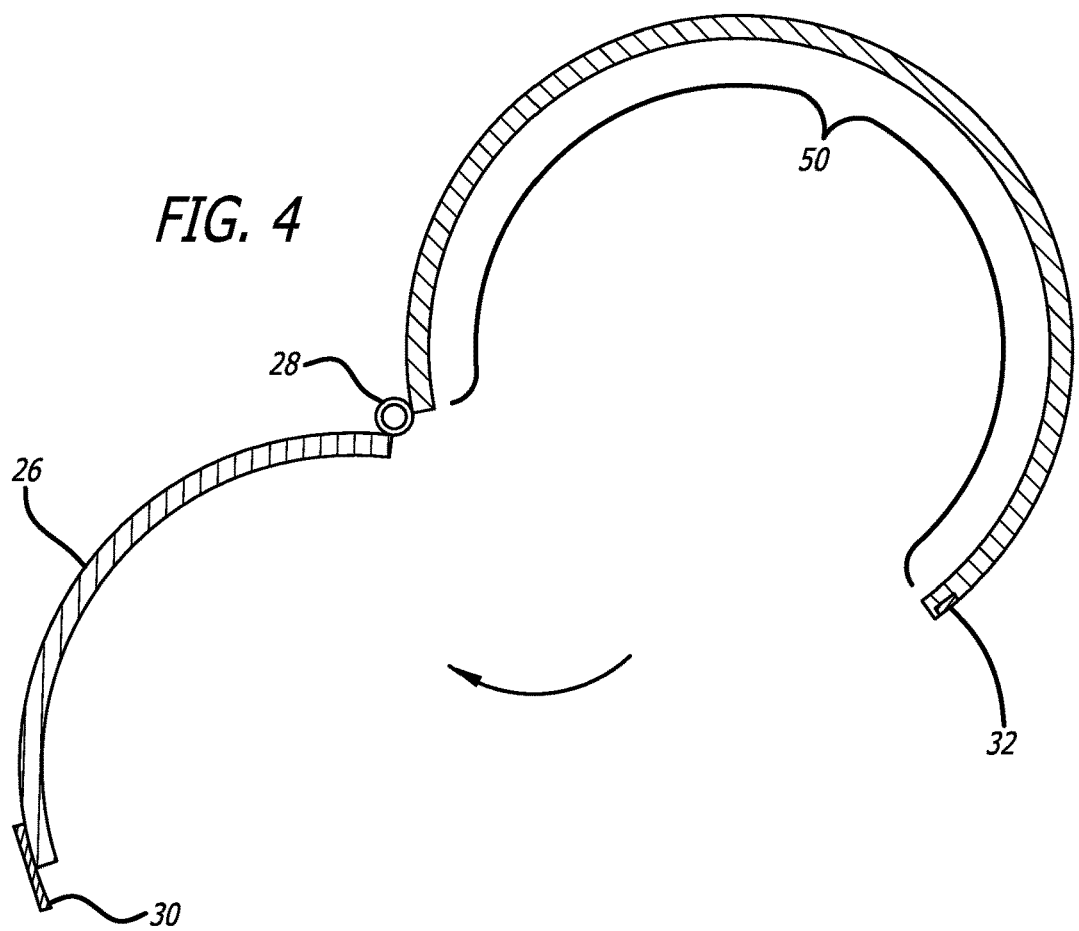
FIG. 4 is a cross sectional view of the embodiment of FIG. 2 taken along line 4-4.
Figure 5:
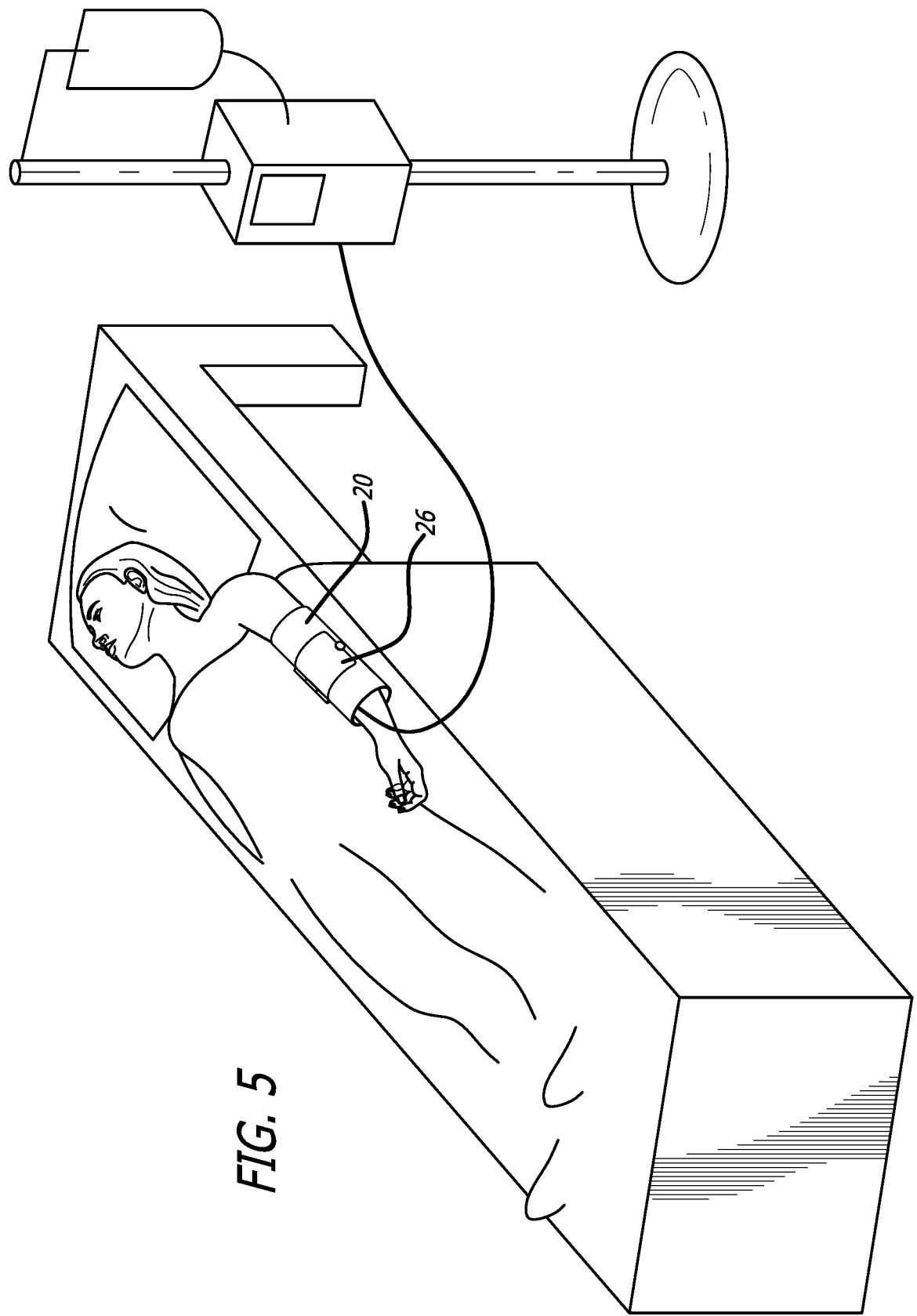
FIG. 5 is a perspective view of the embodiment of FIG. 1 on a patient in the closed configuration.
Figure 6:
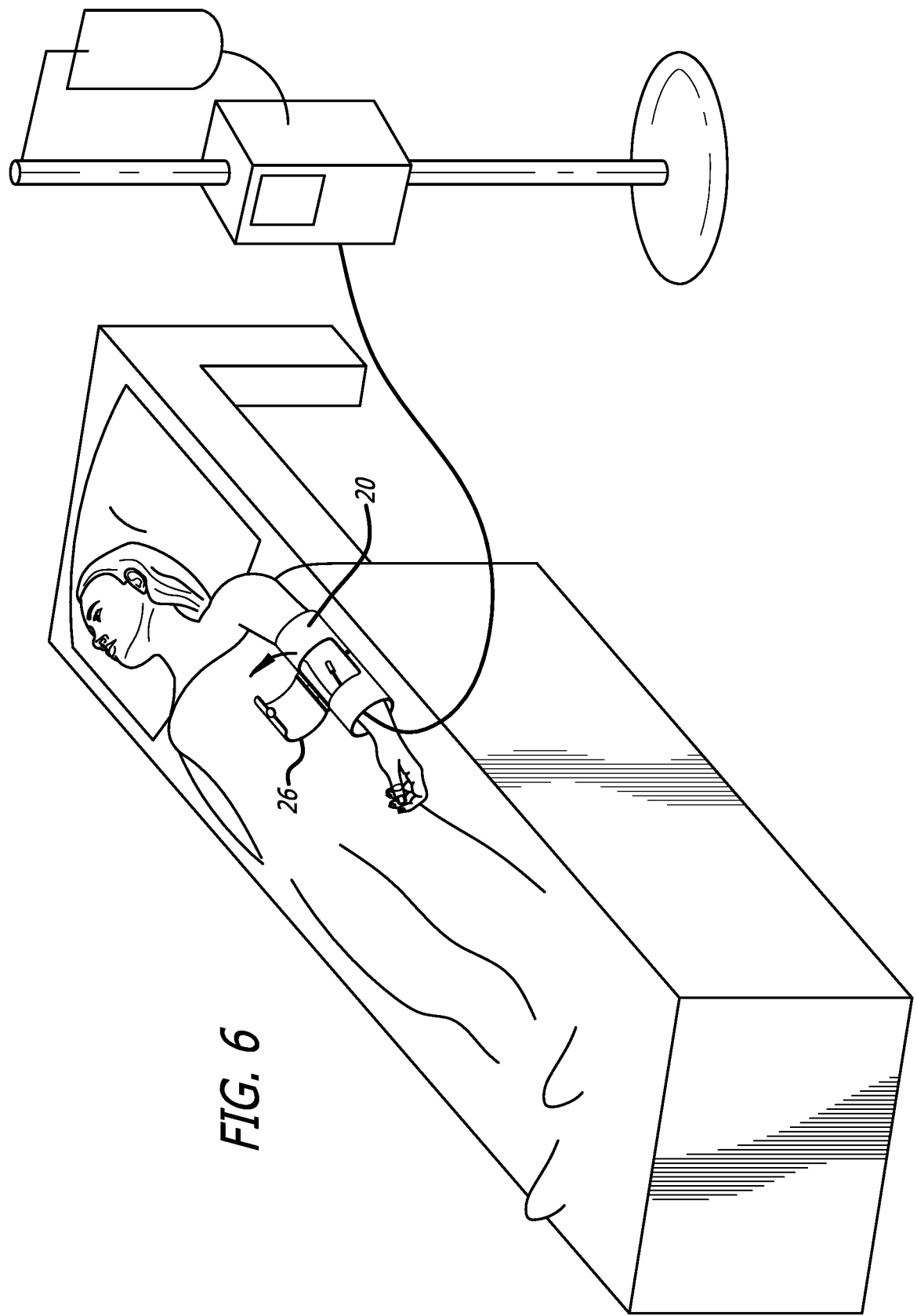
FIG. 6 is a perspective view of the embodiment of FIG. 2 on a patient in the open configuration.

To protect the patient's forearm and wrist and the site of the IV, the present invention as shown in FIGS. 1-6 provides a lightweight tubular sleeve 20 that resists or prevents bending of the elbow more than a few degrees. The sleeve 20 is a thin-walled structure that preferably has some flexibility but is substantially rigid, that is either cylindrical or may include a taper from a wider end 22 to a narrower end 24. To permit access and inspection of the patient's injection site, a door 26 mounted on a hinge 28 is located at a central portion of the sleeve 20. A small magnet 30 can be provided on the door 26 at the free edge that engages with a metal fastener 32 or metal plate to maintain closure of the door 26. The door 26 conforms with the contour of the sleeve 20, and the hinge 28 is arranged longitudinally to permit the door 26 to swing open and expose the patient's IV site. In one preferred embodiment, the door uses a magnetic latch to secure the door closed that can easily be opened when needed but provides sufficient connection to prevent inadvertent opening of the door 26. In other embodiments, a mechanical latch, detent, hook and loop fastener, or clasp can be used to close the door 26.

In one embodiment, the sleeve 20 includes a plurality of air holes 40 (see FIG. 1) to allow airflow across the sleeve to prevent sweat, heat, and moisture from accumulating inside the sleeve. In some embodiments, the sleeve could be made of a thin walled stainless steel tube to facilitate certain sterilization techniques and to extend the life of the sleeve. The sleeve can be reused once sterilized and different sizes would be available to accommodate different sized patients. Once in place, the patent is less likely to accidentally dislodge the IV or impair the flow of IV fluids, and during sleep the patient need not worry about injuring himself or herself with the IV needle. The inner wall of the tube could also include padding 50 (see FIG. 4) in the case of long-term use to improve the comfort of the device.

While certain preferred embodiments have been described and depicted herein and in the drawings, it is understood that the invention is not limited to those depictions and descriptions unless specifically so expressed. Rather, a person of ordinary skill in the art will readily appreciate certain modifications, substitutions, and variations and the invention is intended to include all such modifications, substitutions, and variations. Accordingly, the scope of the claims are properly determined by the appended claims using their customary and ordinary meanings, consistent with but not limited by the descriptions and depictions herein.

I claim:

1. A medical sleeve for a patient with an intravenous injection, comprising:

a rigid plastic cylinder tapered in the longitudinal direction, the rigid plastic cylinder having a first and a second end and a middle portion, the first end having a plurality of circumferentially spaced holes of three rows and the second end having a plurality of circumferentially spaced holes of three rows, and where the middle portion has no rows of holes;

a door in the rigid plastic cylinder at said middle portion, the door connected via a cylindrical hinge on an exterior surface of the rigid plastic cylinder and arranged on a longitudinal direction, the door positioned to provide access to the intravenous injection site; and a circular magnet disposed on an edge of the door on an exterior surface, the circular magnet mounted so that a portion of the circular magnet extends beyond the edge of the door;

a metal fastener inset and mounted at an external surface of the rigid plastic cylinder at a location whereby a portion of the circular magnet that extends beyond the edge of the door makes contact with the metal fastener when the door is closed; and wherein the sleeve is tapered from a proximal end to a distal end.

2. The medical sleeve of claim 1, wherein the thin-walled tubular element is formed of polyvinyl chloride (PVC).

3. The medical sleeve of claim 1, wherein the medical sleeve is reusable.

\* \* \* \* \*